United States Patent [19]
Knuebel et al.

[11] Patent Number: 5,922,670
[45] Date of Patent: Jul. 13, 1999

[54] DIMERIC ALCOHOL-BIS AND TRIMERIC ALCOHOL-TRIS-SULPHATES AND ETHER SULPHATES THEREOF

[75] Inventors: Georg Knuebel, Duesseldorf; Alfred Westfechtel, Hilden; Gerhard Hermanns, Monheim; Rainer Hoffmann, Duesseldorf; Hans-Christian Raths, Monheim, all of Germany

[73] Assignee: Henkel Kommanditgesellschaft auf Aktien, Duesseldorf, Germany

[21] Appl. No.: 08/875,719

[22] PCT Filed: Jan. 23, 1996

[86] PCT No.: PCT/EP96/00259

§ 371 Date: Oct. 1, 1997

§ 102(e) Date: Oct. 1, 1997

[87] PCT Pub. No.: WO96/23768

PCT Pub. Date: Aug. 8, 1996

[30] Foreign Application Priority Data

Feb. 1, 1995 [DE] Germany .................. 195 03 061

[51] Int. Cl.$^6$ ................ C11D 1/12; C11D 1/29
[52] U.S. Cl. .................. 510/426; 558/20; 558/38; 558/44; 558/34; 510/127; 510/290; 510/351; 510/352; 510/357; 510/358; 510/414; 510/424; 510/429; 510/495; 510/498
[58] Field of Search .................. 558/20, 38, 44, 558/34; 510/127, 290, 351, 352, 357, 358, 414, 424, 426, 429, 495, 498

[56] References Cited

U.S. PATENT DOCUMENTS

| | | | |
|---|---|---|---|
| 1,968,797 | 7/1934 | Bertsch | 260/99.12 |
| 4,024,078 | 5/1977 | Gilbert et al. | 252/551 |
| 4,217,296 | 8/1980 | Berkowitz | 260/458 R |
| 4,269,786 | 5/1981 | Berkowitz | 260/458 R |
| 4,735,735 | 4/1988 | Borggrefe et al. | 252/33 |
| 4,765,926 | 8/1988 | Plummer | 252/352 |
| 4,832,876 | 5/1989 | Ahmed | 260/400 |
| 5,117,032 | 5/1992 | Fabry et al. | 558/34 |
| 5,290,484 | 3/1994 | Lutz | 252/549 |
| 5,811,384 | 9/1998 | Tracy et al. | 510/424 |
| 5,846,923 | 12/1998 | Reierson | 510/467 |

FOREIGN PATENT DOCUMENTS

0 247 467 12/1987 European Pat. Off. .
0 401 642 12/1990 European Pat. Off. .

OTHER PUBLICATIONS

M. Rosen, Chemtech, pp. 30–33 (Mar. 1993).
J. Am. Chem. Soc. 115:10083–90 (1993).
A. Hinze, Fette & Öle, pp. 47–51 (1994).

*Primary Examiner*—Mark Kopec
*Assistant Examiner*—Charles Boyer
*Attorney, Agent, or Firm*—Ernest G. Szoke; Wayne C. Jaeschke; Real J. Grandmaison

[57] ABSTRACT

Dimer alcohol bis-sulfates, trimer alcohol tris-sulfates and ether sulfates thereof are prepared by reacting dimer alcohols, trimer alcohols, or alkylene oxide adducts thereof with a sulfating agent, and then neutralizing the reaction product with an aqueous base material.

12 Claims, No Drawings

DIMERIC ALCOHOL-BIS AND TRIMERIC ALCOHOL-TRIS-SULPHATES AND ETHER SULPHATES THEREOF

BACKGROUND OF THE INVENTION

1. Field of the Invention

This invention relates to dimer alcohol bis- and trimer alcohol tris-sulfates and ether sulfates, to a process for their production by reaction of dimer and trimer alcohols with sulfating agents and subsequent neutralization and to their use as surface-active substances and as liquefiers for pastes.

DISCUSSION OF RELATED ART

2. Prior Art

Gemini surfactants are compounds which have two hydrophilic groups and two hydrophobic groups per molecule. These groups are generally separated from one another by a so-called spacer. This spacer is usually a carbon chain which should be long enough to create a sufficient distance between the hydrophilic groups for them to be able to act independently of one another (cf. M. Rosen, Chemtech (1993), pages 20 et seq; F. Menger, C. A. Littau, J. Am. Chem. Soc. 115 (1993), pp. 10083 et seq).

The surfactants described in the cited literature references are distinguished by an unusually low critical micelle concentration and by their ability drastically to reduce the surface tension of water. Unfortunately, these surfactants are difficult to synthesize and, in some cases, can only be obtained by multistage syntheses. The complicated synthesis pathways inevitably lead to relatively high costs which is a disadvantage for application and use on an industrial scale.

The problem addressed by the present invention was to provide a process for the production of new Gemini surfactants which would enable these surfactants to be simply and inexpensively obtained in high yields.

DESCRIPTION OF THE INVENTION

The present invention relates to dimer alcohol bis-sulfates and trimer alcohol tris-sulfates and ether sulfates which are obtainable by reaction of dimer alcohols and/or trimer alcohols or addition products thereof with alkylene oxides with a sulfating agent and subsequent neutralization with an aqueous base.

It has surprisingly been found that, in the sulfation of dimer and trimer alcohols or alkoxylates thereof, the corresponding bis-sulfates and tris-sulfates are obtained in high yields and with high degrees of sulfation. The compounds obtained are so-called Gemini surfactants, the two anionic sulfate groups generally being spaced about 18 carbon atoms apart which ensures that these two hydrophilic groups are able to act independently of one another.

The present invention also relates to a process for the production of dimer alcohol bis-sulfates and trimer alcohol tris-sulfates and ether sulfates, characterized in that dimer alcohols and/or trimer alcohols or addition products thereof with alkylene oxides are reacted with a sulfating agent and the product of this reaction is neutralized with an aqueous base.

Dimer and Trimer Alcohols

The dimer and trimer alcohols used in accordance with the invention are commercially available compounds and may be obtained, for example, by reduction of dimer and trimer fatty acid esters. The dimer and trimer fatty acids themselves may be obtained, for example, by oligomerization of unsaturated fatty acids. The dimer and trimer fatty acids are generally mixtures of acyclic and cyclic dicarboxylic acids containing on average 36 to 44 carbon atoms [cf. A. Hinze in Fette & Öle, 26 (1994)].

Dimer and Trimer Alcohol Alkoxylates

The dimer and trimer alcohol alkoxylates used as starting compounds may be obtained in known manner by alkoxylation of the dimer and trimer alcohols. The alkoxylates preferably used include, for example, the ethoxylates and propoxylates or adducts containing both ethoxy groups and propoxy groups in the molecule. A particularly preferred embodiment of the invention is characterized by the use of adducts containing an average of 1 to 20 moles of ethylene oxide per OH group and, optionally, an average of 1 to 5 moles of propylene oxide per mole of alcohol. The degrees of alkoxylation mentioned are statistical mean values which, for a special product, may be a whole number or a broken number. Preferred dimer and trimer alcohol alkoxylates have a narrow homolog distribution (narrow range ethoxylates, NRE).

To carry out the process according to the invention, the dimer and trimer alcohols or alkoxylates thereof are normally introduced into a reactor. The reaction leading to the dimer or trimer alcohol bis-sulfate may then be carried out by continuous introduction of the sulfating agent.

The sulfation of the dimer and trimer alcohols or alkoxylates thereof may be carried out with standard sulfating agents, for example sulfuric acid, oleum, chlorosulfonic acid, aminosulfonic acid and gaseous sulfur trioxide in admixture with an inert gas, chlorosulfonic acid and gaseous sulfur trioxide being preferred. Where sulfur trioxide is used, it is diluted with air or nitrogen, a gas mixture containing about 1 to 8% by volume and, more particularly, 3 to 5% by volume of sulfur trioxide preferably being used. The molar ratio of OH groups in the starting compounds to sulfating agent may be from 1:0.95 to 1:1.8 and is preferably from 1:1.0 to 1:1.3. The sulfation reaction is normally carried out at 20 to 98° C. With regard to the viscosity of the starting compounds on the one hand and the color quality of the resulting sulfation products on the other hand, temperatures in the range from 25 to 70° C. have proved to be optimal.

The acidic crude sulfated product obtained in the sulfation step is then neutralized with a base and preferably adjusted to a pH value below 9 and more preferably to a pH value of 6.5 to 8.5. A pH value above 9.5 should be avoided. It has been found that, at very high pH values, the ester bond is unstable and serious saponification occurs even if the recommended pH values are only briefly exceeded. Suitable bases for the neutralization step are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_{2-4}$ alkanolamines, for example mono-, di- and triethanolamine, and primary, secondary or tertiary $C_{1-4}$ alkyl amines. The neutralization bases are preferably used in the form of 5 to 55% by weight aqueous solutions, 5 to 25% by weight aqueous sodium hydroxide solutions being preferred.

After the neutralization step, the sulfation products may be bleached in known manner by addition of hydrogen peroxide or sodium hypochlorite solution. Based on the solids content of the sulfation products in the solution, quantities of 0.2 to 2% by weight of hydrogen peroxide, expressed as 100% by weight substance, or corresponding quantities of sodium hypochlorite are used. The pH value of the solutions may be kept constant using suitable buffers, for example sodium phosphate or citric acid. In addition, the use of preservatives, for example formaldehyde solution, p-hydroxybenzoate, sorbic acid or other known preservatives, is recommended for stabilization against bacterial contamination.

COMMERCIAL APPLICATIONS

The dimer alcohol bis-sulfates and trimer alcohol tris-sulfates and ether sulfates have surface-active properties. For example, they promote the wetting of solid surfaces and the emulsification of otherwise immiscible phases.

Accordingly, the present invention also relates to the use of the compounds according to the invention for the production of laundry detergents, dishwashing detergents, cleaners and fabric softeners and hair-care and body-care formulations in which they may be present in quantities of 1 to 50% by weight and preferably 5 to 30% by weight, based on the particular product.

The compounds according to the invention have also been found to be suitable as paste liquefiers for high-viscosity surfactant systems. High-viscosity surfactant systems, for example liquid surfactant pastes with a surfactant content of more than 40% by weight, are normally thick pastes. The addition of the compounds according to the invention to such surfactant pastes produces a distinct improvement in flow behavior.

Accordingly, the present invention also relates to the use of the compounds according to the invention as liquefiers for pastes, more particularly for high-viscosity surfactant systems. The compounds according to the invention are preferably added to the surfactant pastes in a quantity of 1% by weight to 10% by weight, based on the weight of the surfactant paste. If the compounds according to the invention are used in a quantity below 0.5% by weight, an inadequate improvement in flow behavior is generally obtained.

The invention is illustrated by the following Examples.

EXAMPLES

Production of $C_{36}$ Dimer Alcohol Bis-Sulfate (Disodium Salt)

General procedure:

Using a nitrogen stream of about 750 l/h, a product stream of 10 g/min. was introduced into a laboratory continuous falling-film reactor (reactor dimensions: length 110 cm, internal diameter: 0.6 cm) preceded by an oleum evaporator. (The virtual molecular weight was determined from the OH value of the starting product.) At the same time, 65% by weight oleum was pumped into the evaporator at a rate of 1.05 mole equivalents per OH group. The sulfur trioxide formed was driven out of the evaporator with a 250 l/h stream of nitrogen and was also transferred to the reactor. The reactor was temperature-controlled with water (30° C.). The sulfuric acid semiester formed was degassed at the reactor exit and transferred to a glass beaker in which it was neutralized with 25% by weight sodium hydroxide added continuously with vigorous stirring and cooling with ice.

The characteristic data of the surfactant pastes thus obtained were determined by the "DGF Einheitsmethoden" and are shown under the individual compounds. For further analytical investigations, the surfactant pastes were freeze-dried in vacuo.

Sulfation of Dimer Alcohol

Sovermol RPOL 900 (a product of Henkel KGaA, Düsseldorf) as the starting compound was preheated to a temperature of 80° C. to melt the starting product. After the reaction, the reaction product was post-hydrolyzed in a steam bath for another two hours during which the pH value was kept at 7 to 9 with a few drops of NaOH.

Characteristic data of the $C_{36}$ dimer alcohol bis-sulfate (disodium salt):

| | |
|---|---|
| Dry residue (DR): | 31% by weight |
| Unsulfated components (US): | 1.2% by weight |
| Degree of sulfation (S°): | 96% by weight |
| Sodium sulfate: | 1.2% by weight |
| Organically bound sulfur: | 2.2% by weight (corresponds to 2.1 moles S per mole of disulfate) |

Use of the $C_{36}$ Dimer Alcohol Bis-Sulfate (Disodium Salt) as a Paste Liquefier The flow-improving effect was investigated by addition of the compound obtained to a surfactant paste containing 65% by weight of $C_{12-14}$ fatty alcohol x 2 EO sulfate Na salt at a temperature of 25° C.

The results set out in the following Table show that even a small addition of 1% by weight of the compound according to the invention is sufficient to obtain a distinct improvement in the flow properties of the surfactant paste.

What is claimed is:

1. The process of producing dimer alcohol bis-sulfates, trimer alcohol tris-sulfates and ether sulfates thereof, comprising reacting dimer alcohols, trimer alcohols, or alkylene oxide adducts thereof containing an average of 36 to 44 carbon atoms with a sulfating agent, and neutralizing the reaction product with an aqueous base material.

2. A process as in claim 1 wherein said sulfating agent is selected from the group consisting of gaseous sulfur trioxide and chlorosulfonic acid.

3. A process as in claim 1 wherein said reacting with a sulfating agent is carried out with a molar ratio per OH group of said dimer alcohols, trimer alcohols, or alkylene oxide adducts thereof to said sulfating agent of 1:0.95 to 1:1.8.

4. A process as in claim 1 wherein said reacting with a sulfating agent is carried out at a temperature of 20° C. to 98° C.

5. A process as in claim 1 wherein said neutralizing is carried out with a 5% to 55% by weight aqueous base material selected from the group consisting of alkali metal hydroxides, alkaline earth metal oxides and hydroxides, ammonia, mono-, di-, and tri-$C_2$–$C_4$ alkanolamines, and primary, secondary and tertiary $C_1$–$C_4$ alkyl amines.

6. Dimer alcohol bis-sulfates, trimer alcohol tris-sulfates and ether sulfates thereof prepared by reacting dimer alcohols, trimer alcohols, or alkylene oxide adducts thereof containing an average of 36 to 44 carbon atoms with a sulfating agent, and neutralizing the reaction product with an aqueous base material.

7. Dimer alcohol bis-sulfates, trimer alcohol tris-sulfates and ether sulfates thereof as in claim 6 wherein said sulfating agent is selected from the group consisting of gaseous sulfur trioxide and chlorosulfonic acid.

8. Dimer alcohol bis-sulfates, trimer alcohol tris-sulfates and ether sulfates thereof as in claim 6 wherein said reacting with a sulfating agent is carried out with a molar ratio per OH group of said dimer alcohols, trimer alcohols, or alkylene oxide adducts thereof to said sulfating agent of 1:0.95 to 1:1.8.

9. Dimer alcohol bis-sulfates, trimer alcohol tris-sulfates and ether sulfates thereof as in claim 6 wherein said reacting with a sulfating agent is carried out at a temperature of 20° C. to 98° C.

10. Dimer alcohol bis-sulfates, trimer alcohol tris-sulfates and ether sulfates thereof as in claim 6 wherein said neutralizing is carried out with a 5% to 55% by weight aqueous base material selected from the group consisting of alkali metal hydroxides, alkaline earth metal oxides and hydroxides, ammonia, mono-, di-, and tri-$C_2$–$C_4$ alkanolamines, and primary, secondary and tertiary $C_1$–$C_4$ alkyl amines.

11. A cleaning composition containing the product of claim 6.

12. The process of reducing the viscosity of a viscous liquid surfactant composition comprising adding thereto the product of claim 6.

* * * * *